US008679167B2

(12) United States Patent
Tipirneni et al.

(10) Patent No.: US 8,679,167 B2
(45) Date of Patent: Mar. 25, 2014

(54) SYSTEM AND METHOD FOR A CAP USED IN THE FIXATION OF BONE FRACTURES

(75) Inventors: Kishore Tipirneni, Glendale, AZ (US); Wayne Vassello, Lake Worth, FL (US)

(73) Assignee: Orthoip, LLC, Boca Raton, FL (US)

( * ) Notice: Subject to any disclaimer, the term of this patent is extended or adjusted under 35 U.S.C. 154(b) by 928 days.

(21) Appl. No.: 11/678,473

(22) Filed: Feb. 23, 2007

(65) Prior Publication Data

US 2007/0162026 A1    Jul. 12, 2007

Related U.S. Application Data

(63) Continuation-in-part of application No. 10/779,892, filed on Feb. 17, 2004, which is a continuation of application No. 10/272,773, filed on Oct. 17, 2002, now Pat. No. 6,736,819.

(60) Provisional application No. 60/330,187, filed on Oct. 18, 2001.

(51) Int. Cl.
*A61B 17/84* (2006.01)
(52) U.S. Cl.
USPC .......................................... 606/305; 606/300
(58) Field of Classification Search
USPC .................... 606/65, 300, 301, 305; 411/389
See application file for complete search history.

(56) References Cited

U.S. PATENT DOCUMENTS

| 1,025,008 | A |   | 4/1912  | Miner         |        |
|-----------|---|---|---------|---------------|--------|
| 2,077,804 | A |   | 4/1937  | Morrison      |        |
| 2,381,050 | A |   | 8/1945  | Hardinge      |        |
| 2,397,545 | A |   | 4/1946  | Hardinge      |        |
| 2,414,882 | A |   | 1/1947  | Longfellow    |        |
| 2,490,364 | A |   | 12/1949 | Livingston    |        |
| 2,511,051 | A | * | 6/1950  | Dzus ........... | 81/451 |
| 3,051,169 | A |   | 8/1962  | Gustaf-Bertil |        |
| 3,433,220 | A |   | 3/1969  | Zickel        |        |

(Continued)

FOREIGN PATENT DOCUMENTS

| FR | 2784019     | 4/2000  |
|----|-------------|---------|
| WO | WO00067652  | 11/2000 |
| WO | WO2007125561| 11/2008 |
| WO | WO2009015075| 12/2009 |

OTHER PUBLICATIONS

Notice of Allowance mailed Feb. 20, 2004 in U.S. Appl. No. 10/272,773.

(Continued)

*Primary Examiner* — Christian Sevilla
(74) *Attorney, Agent, or Firm* — Snell & Wilmer L.L.P.

(57) ABSTRACT

A system and method for facilitating the fixation of bone fractures is disclosed. The head component includes a tip, cutting threads and mating threads which are inserted into the far cortex of the bone. A wire extends from the head component and exits from the near cortex. A cap device includes a tension spring, wherein the tension spring is configured to assert friction against the wire when the cap is translated in one direction, but minimal friction against the wire when the cap is translated in the opposite direction. The cap is threaded over the wire such that the cap is restricted from backwards movement. Tension is then applied to the wire while the cap is tightened against or within the bone surface to apply an appropriate amount of pressure between the surfaces of the fracture. The excess wire beyond the cap can then be removed.

12 Claims, 9 Drawing Sheets

(56) References Cited

U.S. PATENT DOCUMENTS

| | | |
|---|---|---|
| 3,489,143 A | 1/1970 | Halloran |
| 4,456,005 A | 6/1984 | Lichty |
| 4,617,922 A | 10/1986 | Griggs |
| 4,621,629 A * | 11/1986 | Koeneman ............... 606/65 |
| 4,632,100 A | 12/1986 | Somers et al. |
| 4,640,271 A | 2/1987 | Lower |
| 4,708,132 A | 11/1987 | Silvestrini |
| 4,741,330 A | 5/1988 | Hayhurst |
| 4,773,406 A | 9/1988 | Spector et al. |
| 4,858,601 A | 8/1989 | Glisson |
| 4,863,383 A | 9/1989 | Grafelmann |
| 4,889,110 A | 12/1989 | Galline |
| 4,905,680 A | 3/1990 | Tunc |
| 4,934,935 A | 6/1990 | Edwards |
| 4,940,467 A | 7/1990 | Tronzo |
| 4,959,064 A * | 9/1990 | Engelhardt ............... 606/65 |
| 5,019,079 A | 5/1991 | Ross |
| 5,041,116 A | 8/1991 | Wilson |
| 5,061,137 A | 10/1991 | Gourd |
| 5,100,405 A | 3/1992 | McLaren |
| 5,102,276 A | 4/1992 | Gourd |
| 5,116,336 A | 5/1992 | Frigg |
| 5,116,340 A | 5/1992 | Songer |
| 5,122,133 A | 6/1992 | Evans |
| 5,127,914 A | 7/1992 | Calderale et al. |
| 5,129,901 A | 7/1992 | Decoste |
| 5,141,520 A * | 8/1992 | Goble et al. ............... 606/232 |
| 5,207,753 A | 5/1993 | Badrinath |
| 5,217,462 A * | 6/1993 | Asnis et al. ............... 606/916 |
| 5,269,784 A | 12/1993 | Mast |
| 5,300,075 A | 4/1994 | Gordon |
| 5,306,290 A | 4/1994 | Martins |
| 5,324,292 A | 6/1994 | Meyers |
| 5,336,028 A | 8/1994 | Yamamoto |
| 5,338,139 A | 8/1994 | Swanstrom |
| 5,364,398 A | 11/1994 | Chapman et al. |
| 5,368,605 A | 11/1994 | Miller |
| 5,382,124 A | 1/1995 | Frattarola |
| 5,409,493 A | 4/1995 | Greenberg |
| 5,417,692 A | 5/1995 | Goble et al. |
| 5,423,820 A | 6/1995 | Miller |
| 5,431,660 A | 7/1995 | Burke |
| 5,462,547 A | 10/1995 | Weigum |
| 5,507,801 A | 4/1996 | Gisin |
| 5,520,691 A | 5/1996 | Branch |
| 5,586,985 A | 12/1996 | Putnam et al. |
| 5,591,207 A | 1/1997 | Coleman |
| 5,601,553 A | 2/1997 | Trebing et al. |
| 5,607,426 A | 3/1997 | Ralph et al. |
| 5,611,801 A | 3/1997 | Songer |
| 5,632,745 A | 5/1997 | Schwartz |
| 5,643,267 A | 7/1997 | Hitomi et al. |
| 5,702,397 A | 12/1997 | Goble |
| 5,709,687 A | 1/1998 | Pennig |
| 5,725,582 A | 3/1998 | Bevan |
| 5,809,849 A | 9/1998 | Coffey et al. |
| 5,810,821 A | 9/1998 | Vandewalle |
| 5,827,285 A | 10/1998 | Bramlet |
| 5,893,850 A * | 4/1999 | Cachia ............... 606/326 |
| 5,893,859 A | 4/1999 | Marin et al. |
| 5,899,906 A | 5/1999 | Schenk |
| 5,902,011 A | 5/1999 | Hand et al. |
| 5,928,236 A | 7/1999 | Augagneur et al. |
| 5,954,722 A * | 9/1999 | Bono ............... 606/281 |
| 5,964,760 A | 10/1999 | Richelsoph |
| 5,964,763 A | 10/1999 | Incavo et al. |
| 5,976,139 A | 11/1999 | Bramlet |
| 5,984,925 A | 11/1999 | Apgar |
| 5,993,477 A * | 11/1999 | Vaitekunas et al. ........ 606/232 |
| 5,997,538 A | 12/1999 | Asnis et al. |
| 5,997,541 A | 12/1999 | Schenk |
| 6,027,523 A | 2/2000 | Schmieding |
| 6,033,429 A | 3/2000 | Magovern |
| 6,039,740 A | 3/2000 | Olerud |
| 6,050,998 A | 4/2000 | Fletcher |
| 6,093,188 A | 7/2000 | Murray |
| 6,143,037 A | 11/2000 | Goldstein et al. |
| 6,171,310 B1 | 1/2001 | Giordano |
| 6,174,006 B1 | 1/2001 | Burt |
| 6,183,474 B1 | 2/2001 | Bramlet |
| 6,235,062 B1 | 5/2001 | Grammas |
| 6,245,071 B1 | 6/2001 | Pierson |
| 6,251,111 B1 | 6/2001 | Barker et al. |
| 6,319,254 B1 | 11/2001 | Giet et al. |
| 6,348,053 B1 | 2/2002 | Cachia |
| 6,368,326 B1 * | 4/2002 | Dakin et al. ............... 606/103 |
| 6,524,313 B1 | 2/2003 | Fassier et al. |
| 6,602,293 B1 | 8/2003 | Biermann et al. |
| 6,605,090 B1 | 8/2003 | Trieu et al. |
| 6,610,067 B2 | 8/2003 | Tallarida et al. |
| 6,629,534 B1 | 10/2003 | St Goar et al. |
| 6,632,224 B2 | 10/2003 | Cachia |
| 6,656,184 B1 | 12/2003 | White et al. |
| 6,656,185 B2 | 12/2003 | Gleason |
| 6,685,706 B2 | 2/2004 | Padget et al. |
| 6,695,844 B2 | 2/2004 | Bramlet |
| 6,736,819 B2 | 5/2004 | Tipirneni |
| 6,840,953 B2 | 1/2005 | Martinek |
| 6,887,243 B2 | 5/2005 | Culbert |
| 6,887,271 B2 | 5/2005 | Justin et al. |
| 6,890,333 B2 | 5/2005 | von Hoffmann et al. |
| 6,902,567 B2 | 6/2005 | Del Medico |
| 6,908,465 B2 | 6/2005 | von Hoffmann et al. |
| 6,984,241 B2 | 1/2006 | Lubbers et al. |
| 7,008,428 B2 | 3/2006 | Cachia |
| 7,033,363 B2 | 4/2006 | Powell |
| 7,070,601 B2 | 7/2006 | Culbert et al. |
| 7,090,686 B2 | 8/2006 | Nobles et al. |
| 7,094,239 B1 | 8/2006 | Michelson |
| 7,094,240 B2 | 8/2006 | Molz et al. |
| 7,135,023 B2 | 11/2006 | Watkins et al. |
| 7,147,639 B2 | 12/2006 | Berki et al. |
| 7,163,542 B2 | 1/2007 | Ryan |
| 7,172,595 B1 | 2/2007 | Goble |
| 7,189,251 B2 | 3/2007 | Kay |
| 7,476,254 B2 | 1/2009 | White et al. |
| 7,591,823 B2 | 9/2009 | Tipirneni |
| 7,641,677 B2 | 1/2010 | Weiner et al. |
| 7,771,428 B2 | 8/2010 | Siravo et al. |
| 2002/0198527 A1 | 12/2002 | Muckter |
| 2003/0036761 A1 | 2/2003 | Smothers et al. |
| 2003/0083658 A1 | 5/2003 | Hawkes et al. |
| 2003/0187440 A1 | 10/2003 | Richelsoph et al. |
| 2003/0216780 A1 | 11/2003 | Fitts et al. |
| 2004/0097943 A1 | 5/2004 | Hart |
| 2004/0127906 A1 | 7/2004 | Culbert et al. |
| 2004/0236424 A1 | 11/2004 | Berez et al. |
| 2004/0243129 A1 | 12/2004 | Moumene et al. |
| 2005/0010226 A1 | 1/2005 | Grady, Jr. et al. |
| 2005/0234456 A1 | 10/2005 | Malandain |
| 2005/0263549 A1 | 12/2005 | Scheiner |
| 2006/0129148 A1 | 6/2006 | Simmons et al. |
| 2006/0147127 A1 | 7/2006 | Slavin |
| 2006/0161805 A1 | 7/2006 | Tseng |
| 2006/0167457 A1 | 7/2006 | Suddaby |
| 2006/0190001 A1 | 8/2006 | Powell |
| 2006/0248638 A1 | 11/2006 | Diethelm et al. |
| 2007/0055249 A1 | 3/2007 | Jensen |
| 2007/0123878 A1 | 5/2007 | Shaver |
| 2007/0162019 A1 | 7/2007 | Burns |
| 2007/0162026 A1 | 7/2007 | Tipirneni et al. |
| 2007/0190230 A1 | 8/2007 | Trieu |
| 2007/0233100 A1 | 10/2007 | Metzinger |
| 2007/0260248 A1 | 11/2007 | Tipirneni |
| 2007/0270847 A1 | 11/2007 | Shaw |
| 2007/0276382 A1 | 11/2007 | Mikhail et al. |
| 2008/0086144 A1 | 4/2008 | Zander |
| 2008/0147126 A1 | 6/2008 | Tipirneni |
| 2008/0147127 A1 | 6/2008 | Tipirneni et al. |
| 2008/0243191 A1 | 10/2008 | Tipirneni et al. |
| 2008/0255555 A1 | 10/2008 | Justis et al. |
| 2008/0255621 A1 | 10/2008 | Fricker et al. |
| 2008/0300636 A1 | 12/2008 | Carli et al. |
| 2009/0131936 A1 | 5/2009 | Tipirneni et al. |

(56) References Cited

U.S. PATENT DOCUMENTS

| | | | |
|---|---|---|---|
| 2009/0131990 | A1 | 5/2009 | Tipirneni et al. |
| 2009/0131991 | A1 | 5/2009 | Tipirneni et al. |
| 2009/0177199 | A1 | 7/2009 | Tipirneni |
| 2009/0198288 | A1 | 8/2009 | Hoof et al. |
| 2009/0254089 | A1 | 10/2009 | Tipirneni |
| 2009/0254129 | A1 | 10/2009 | Tipirneni |
| 2009/0306718 | A1 | 12/2009 | Tipirneni |
| 2010/0114097 | A1 | 5/2010 | Siravo et al. |
| 2010/0312245 | A1 | 12/2010 | Tipirneni et al. |
| 2010/0312292 | A1 | 12/2010 | Tipirneni et al. |
| 2011/0034925 | A1 | 2/2011 | Tipirneni et al. |
| 2011/0295252 | A1 | 12/2011 | Tipirneni et al. |

OTHER PUBLICATIONS

Non-Final Office Action mailed Nov. 16, 2005 in U.S. Appl. No. 10/779,892.
Requirement for Restriction mailed Jul. 18, 2006 in U.S. Appl. No. 10/779,892.
Final Office Action mailed Jan. 3, 2007 in U.S. Appl. No. 10/779,892.
Advisory Action mailed Feb. 2, 2007 in U.S. Appl. No. 10/779,892.
Non-Final Office Action mailed Mar. 1, 2007 in U.S. Appl. No. 10/779,892.
Final Office Action mailed Oct. 31, 2007 in U.S. Appl. No. 10/779,892.
Advisory Action mailed Jan. 22, 2008 in U.S. Appl. No. 10/779,892.
Non-Final Office Action mailed Mar. 4, 2008 in U.S. Appl. No. 10/779,892.
Requirement for Restriction mailed Dec. 10, 2008 in U.S. Appl. No. 10/779,892.
ISR and Written Opinion mailed Jan. 22, 2009 in PCT/US08/84623.
Final Office Action mailed May 14, 2009 in U.S. Appl. No. 10/779,892.
Notice of Allowance mailed Aug. 7, 2009 in U.S. Appl. No. 10/779,892.
Non-Final Office Action mailed Aug. 6, 2009 in U.S. Appl. No. 11/742,457.
Non-Final Office Action mailed Jun. 10, 2009 in U.S. Appl. No. 11/952,413.
Non-Final Office Action mailed Jun. 19, 2009 in U.S. Appl. No. 11/952,715.
USPTO; Notice of Allowance dated Dec. 14, 2010 in U.S. Appl. No. 12/400,184.
PCT; International Preliminary Report on Patentability dated Jul. 15, 2010 in Application No. PCT/US2008/084623.
International Search Report and Written Opinion dated Jul. 7, 2011 in Application No. PCT/US2011/033370.
Notice of Allowance dated Sep. 29, 2011 in U.S. Appl. No. 12/400,165.
Final Office Action dated Oct. 28, 2011 in U.S. Appl. No. 12/369,589.
Office Action dated Nov. 1, 2011 in U.S. Appl. No. 12/425,225.
Office Action dated Nov. 10, 2011 in U.S. Appl. No. 12/491,132.
Office Action dated Nov. 10, 2011 in U.S. Appl. No. 12/258,013.
Office Action dated Sep. 2, 2011 in U.S. Appl. No. 12/104,658.
Final Office Action issued Jan. 22, 2010 in U.S. Appl. No. 11/742,457.
Non-Final Office Action issued Dec. 30, 2009 in U.S. Appl. No. 11/952,413.
Final Office Action issued Jan. 25, 2010 in U.S. Appl. No. 11/952,715.
PCT/US2009/061782 International Search Report and Written Opinion issued Dec. 15, 2009.
PCT/US09/578791 International Search Report and Written Opinion issued Nov. 16, 2009.
International Preliminary Report on Patentability dated Jan. 31, 2011 in Application No. PCT/US2009/061782.
International Preliminary Report on Patentability dated Jan. 31, 2011 in Application No. PCT/US2009/057879.
Office Action dated Mar. 17, 2011 in U.S. Appl. No. 12/104,658.
Office Action dated Mar. 8, 2011 in U.S. Appl. No. 12/104,328.
Office Action dated Apr. 27, 2011 in U.S. Appl. No. 12/400,165.
Office Action dated May 11, 2011 in U.S. Appl. No. 12/369,589.
International Preliminary Report on Patentability dated Jul. 20, 2011 in Application No. PCT/US2010/023537.
Office Action dated Jun. 22, 2011 in U.S. Appl. No. 12/235,405.
Office Action Restriction dated Jun. 22, 2011 in U.S. Appl. No. 12/163,122.
Final Office Action dated Aug. 16, 2011 in U.S. Appl. No. 12/104,328.
Office Action dated Aug. 17, 2011 in U.S. Appl. No. 12/163,122.
Office Action dated Aug. 19, 2011 in U.S. Appl. No. 12/265,890.
Non-Final Office Action issued Jun. 28, 2010 in U.S. Appl. No. 12/400,184.
Final Office Action issued Jun. 29, 2010 in U.S. Appl. No. 11/952,413.
Advisory Action issued Sep. 1, 2010 in U.S. Appl. No. 11/952,413.
PCT International Search Report and Written Opinion dated Jan. 22, 2009.
Final Office Action dated Dec. 7, 2011 in U.S. Appl. No. 12/235,405.
Final Office Action dated Feb. 1, 2012 in U.S. Appl. No. 12/265,890.
Final Office Action mailed Jan. 22, 2010 in U.S. Appl. No. 11/742,457.
Advisory Action mailed Mar. 30, 2010 in U.S. Appl. No. 11/742,457.
Final Office Action mailed Jan. 25, 2010 in U.S. Appl. No. 11/952,715.
Advisory Action mailed on Apr. 12, 2010 in U.S. Appl. No. 11/952,715.
Notice to File Missing Parts on May 12, 2010 in U.S. Appl. No. 12/769,529.
URL: http://www.cayennemedical.com/products/ifix/, Title: iFix, Source: Cayenne Medical.
PCT-US2010-023537 International Search and Written Opinion Report mailed Apr. 15, 2010.

* cited by examiner

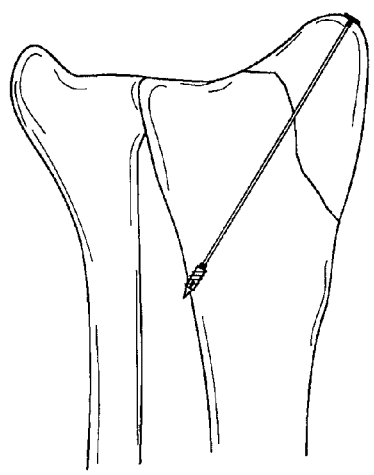
FIG. 4D
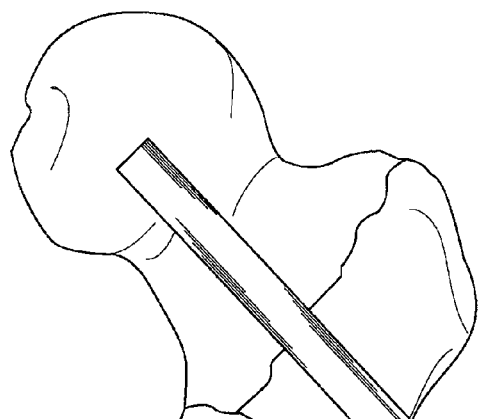
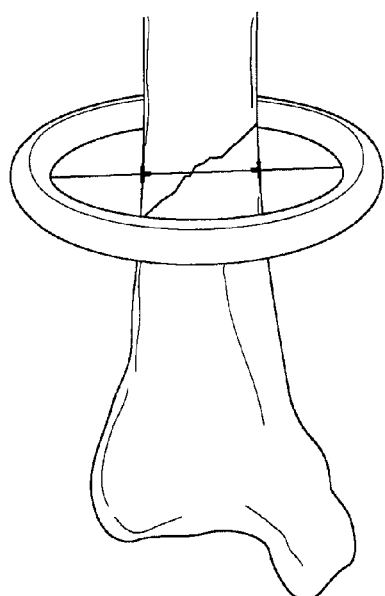
FIG. 4E
FIG. 4F
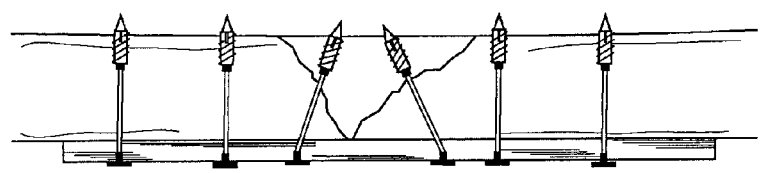
FIG. 4G

SYSTEM AND METHOD FOR A CAP USED IN THE FIXATION OF BONE FRACTURES

CROSS-REFERENCE TO RELATED APPLICATIONS

This application is a continuation-in-part of, and claims priority to, U.S. Ser. No. 10/779,892 filed on Feb. 17, 2004 and entitled SYSTEM AND METHOD FOR THE FIXATION OF BONE FRACTURES which itself claims priority to continuation application U.S. Ser. No. 10/272,773 filed on Oct. 17, 2002 with the same title (now U.S. Pat. No. 6,736,819). The '819 patent itself claims priority to U.S. Provisional Application Ser. No. 60/330,187, entitled LAGWIRE SYSTEM AND METHOD filed Oct. 18, 2001, all of which are incorporated herein by reference.

FIELD OF INVENTION

The invention generally relates to a system and method for the fixation of fractures in one or more objects, and more particularly, to an improved cap used in a lagwire system for the fixation of bone fractures.

BACKGROUND OF THE INVENTION

It is well-known in the medical arts that constant pressure on a bone fracture speeds healing. As such, orthopedic physicians typically insert one or more screws in the area of the fracture in order to assert constant pressure on the bone fracture. However, the insertion of existing screws through or around fractures has disadvantages. For example, the entire process is very time-consuming because inserting a regular screw usually involves multiple steps such as drilling the pilot hole, measuring the relevant distances to determine the appropriate screw selection, tapping the hole to establish threads and screwing the screw into the hole. Moreover, when using a lagscrew, the process usually includes even more steps such as drilling through the near cortex to establish the gliding hole (e.g., 3.5 mm), placing the drill guide in the proper location, drilling through the far cortex (e.g., 2.5 mm), measuring the distance to determine the appropriate screw selection, tapping the hole to establish threads and screwing the screw into the hole, thereby attempting to compress the fracture. Again, each step and the entire process is very time-consuming.

In addition to the length and complexity of the process, the prior art system also typically includes inadequate components. For example, in poor bone, prior art screws often loose their grip and strip out of the bone. Currently available lag screws also typically provide only one side of cortex fixation and are generally not suited for percutaneus surgery. Moreover, when placing the screws in the bone, the physician may not accurately set the screw into the distal hole or may miss the distal hole completely, thereby resulting in the screw stripping the threads or breaking the bone.

Furthermore, the location and extent of most every fracture is unique, so different screws are often needed for each fracture. Because the physician typically is unable to accurately determine the type or size of screw needed until the physician enters the bone and measures the appropriate screw placement, operating facilities need to store and make available large inventories of screws. Particularly, screws usually range in length from about 10 mm to about 75 mm with available screw sizes limited to every 2 mm there between. Moreover, for each size of screw, the screws may be either a cancellous or cortical type, and for each size and type of screw, the screw may include one of three different pitches. Accordingly, a screw set typically exceeds one hundred screws. Furthermore, if cannulated screws are desired, another entire screw set of over one hundred additional screws is often needed. Moreover, each time a screw from a screw set is utilized in a procedure, a replacement screw is typically obtained to complete the set. As such, inventory management of screws is a very large problem for many operating facilities. A need exists for a lagwire system which simplifies and expedites the process for the fixation of bone fractures, while minimizing the number of components needed in the process.

SUMMARY OF THE INVENTION

In general, the invention facilitates the fixation of bone fractures. In one embodiment, the head component includes a tip, cutting threads and mating threads which are inserted into the far cortex of the bone. A wire extends from the head component and exits from the near cortex.

A cap device fits over the other end of the wire such that the cap device permits travel of the cap in one direction (e.g., distal travel with respect to the wire), but resists travel of the cap in the other direction (e.g., proximal travel with respect to the wire). In one embodiment, a cap device having a sawtooth inner surface is threaded over the wire having an inverse sawtooth outer surface such that the cap is restricted from backwards movement. In another embodiment, the cap includes a circular tension spring inside the cap such that the wire is received within a central opening within the circular tension spring. The tension spring also includes a nub extending from the outer circumference of the tension spring such that a portion of the inner circumference of the tension spring provides friction against the wire only one way (when the cap is pulled proximal, away from the bone). The friction is asserted against the wire because the nub on the side of the tension spring hits the top circular cap, so it forces the tension spring to flex and assert friction on the wire. When the cap is pushed the other way (e.g., when the cap is pushed distal, toward the bone) the nub of the tension spring is forced down, so it does not engage any surface, and the wire is able to translate, with minimal or no friction, through the central opening in the tension spring.

Tension is then applied to the wire while the cap is tightened against or within the bone surface to thereby apply an appropriate amount of pressure between the surfaces of the fracture. The excess wire beyond the cap can then be removed.

The invention also includes a system for facilitating a change in distance between objects, wherein the system includes a head component configured to attach to one of the objects; a wire having a first end and a second end, wherein the first end of the wire is configured to mate with the head component; and, a cap configured to mate with the second end of the wire. The invention also includes a method for facilitating a change in distance between a first and second surface. The method includes providing a head component mated with a wire having a first interface component; inserting the head component into the first surface by mating a drill over a driver head of the head component to facilitate drilling the head component into the bone and cutting new threads into the object using the cutting threads and mating the new threads with the mating threads; extending the wire through the second surface; threading a cap having a second interface component over the first interface component of the wire; and removing the excess wire beyond the cap.

BRIEF DESCRIPTION OF THE DRAWINGS

A more complete understanding of the present invention may be derived by referring to the detailed description and claims when considered in connection with the figures, wherein like reference numbers refer to similar elements throughout the figures, and:

FIGS. 4B-4D are fixations of fractures of a certain portions of a bone in accordance with an exemplary embodiment of the present invention.

FIG. 4E is a fixation of a bone fracture by inserting the lagwire through the entire limb to facilitate attaching an external fixation device to the limb in accordance with an exemplary embodiment of the present invention.

FIGS. 4F-4G is a fixation of a bone fracture by inserting the lagwire through the entire limb to facilitate holding a plate to the bone to help fix certain types of fractures in accordance with an exemplary embodiment of the present invention.

DETAILED DESCRIPTION

The present invention is described herein and includes various exemplary embodiments in sufficient detail to enable those skilled in the art to practice the invention, and it should be understood that other embodiments may be realized without departing from the spirit and scope of the invention. Thus, the following detailed description is presented for purposes of illustration only, and not of limitation, and the scope of the invention is defined solely by the appended claims. The particular implementations shown and described herein are illustrative of the invention and its best mode and are not intended to otherwise limit the scope of the present invention in any way.

In general, the present invention facilitates the change in distance between objects or surfaces, compresses objects together and/or provides a configurable or random amount of pressure between surfaces. The system may facilitate changing, maintaining, reducing and/or expanding the distance between objects. The applied pressure may be suitably configured to be constant, increasing, decreasing, variable, random, and/or the like. In an exemplary embodiment, the invention includes a device which may be fixedly or removably attached to pathology, such as to a certain portion of a bone. In a particular embodiment, the device is fixedly or removably attached to the far cortex of the bone. In another embodiment, the invention includes a device or method for retracting the attached device to reduce the distance between the surfaces of the pathology. In a further embodiment, the invention includes a device and/or method for maintaining the pressure between the surfaces of pathology.

Figure 1:
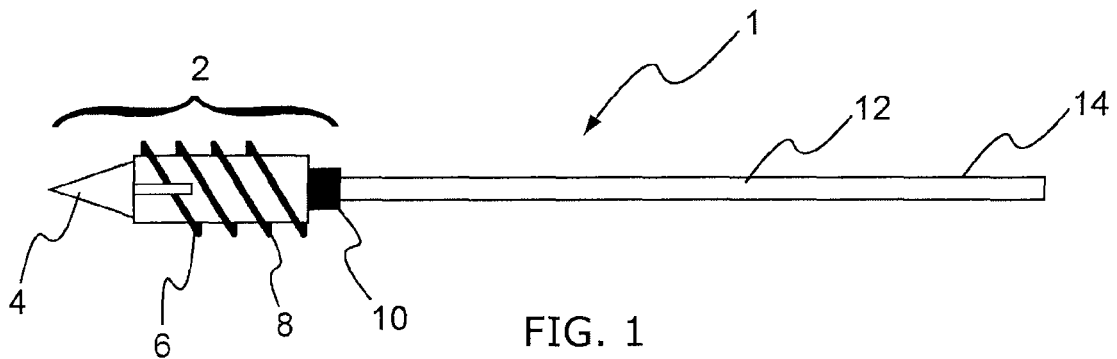
FIG. 1 is a lagwire system including a head component and wire in accordance with an exemplary embodiment of the present invention.

In an exemplary embodiment, and as shown in FIGS. 1 and 2, the lagwire system 1 includes a head component 2, a wire 12 and a cap 20. The lagwire system 1 may be fabricated using any type, amount or combination of materials suitably configured for the particular application. In an exemplary embodiment for medical applications, the lagwire system 1 is fabricated with stainless steel, titanium and/or titanium alloy which minimize reactivity with the body. Each component may be fabricated with various diameters, thread pitches, lengths and/or the like.

Certain exemplary components of the system will now be discussed. The head component 2 is any device which is configured to fixedly or removably attach to any object, such as pathology. In a particular embodiment, the head component 2 is configured to be fixedly or removably attached to the far cortex of the bone, as shown in FIGS. 4A-4G. As best shown in FIG. 1, the head component 2 may include, for example, a self drilling tip 4 device which is suitably configured to puncture a hole and/or guide the head component 2, self cutting threads 6 which are suitably configured to cut thread grooves into the inside surface of a hole, fastening threads 8 which are suitably configured to mate with the newly formed thread grooves, and a tool attachment 10 suitably configured for mating with a tool head (e.g., hex head wrench, socket wrench, Phillips screwdriver, flathead screwdriver, allan wrench and/or the like). Head component 2 may include different thread configurations, lengths, diameters, pitches and the like to facilitate insertion into different types of bone or other structures (e.g., cortical bone, cancellous bone, etc).

In a particular embodiment, the tip is on the front end of head component 2, followed by the cutting threads 6, the fastening threads 8, the tool attachment 10, then wire 12. The elements of head component 2 may be fabricated as one component or one or more elements may be configured to be removably or fixedly mated together to form head component 2. If mated together, a particular element may be exchanged for different applications. For example, if head component 2 needs to be inserted into a dense or hard bone, a stronger or sharper tip 4 may be screwed into thread element 6.8. Moreover, if deeper thread grooves are desired, cutting threads 6 may be replaced with greater diameter threads. Furthermore, if a different tool head is incorporated into a drill, tool attachment 10 may be exchanged with the appropriate attachment.

In one embodiment, the outside diameter of the fastening threads are similar to the thread diameters of known surgical screw sizes. Exemplary outside diameters of cortical head components include 3.5 mm and 4.5 mm, wherein the length of the thread section is similar to the cortex thickness. Exemplary outside diameters of cancellous (i.e., little or no cortex) head components include about 4.0 mm and 6.5 mm, wherein the length of the thread section may be about 16 mm or 32 mm.

Wire 12 is any device suitably configured, when tension is applied, to reduce the distance between two surfaces. In one embodiment, wire 12 is configured to retract the head component 2 device to reduce the distance between the surfaces of the pathology. In one embodiment, head component 2 and wire 12 are constructed as one component. In another embodiment, head component 2 and wire 12 are constructed as separate components, but the components are configured such that the head component 2 may be threaded onto wire 12 after wire 12 is placed into the bone. Wire 12 further includes an interface component 14 on at least a portion of its surface, wherein the interface component 14 is suitably configured to limit the movement of cap 20 to move distally toward head component 2, but not proximally (backwards).

In an exemplary embodiment, interface component 14 of wire 12 includes a sawtooth like configuration such that one side of each tooth (e.g. the side closest to head component 2) is substantially perpendicular to the surface of wire 12, while the other side of the sawtooth is at a suitable angle, such as 45 degrees, thereby forming a triangular pattern for each sawtooth. In this manner, the inverse sawtooth on the inside surface of the cap slides or bends over the angled side of the wire sawtooth, but the substantially perpendicular side of the wire sawtooth restricts or limits the cap sawtooth from backwards movement. In another embodiment, any portion or the entire length of wire 12 includes any configuration such as, for example, round, oval, flat on one or more portions of the wire, and/or microgrooves or ridges along the wire (which may include the sawtooth configuration, indentions or other configurations) to increase the friction along the wire. In one embodiment, wire 12 holds 20 pounds of pull; however, microgrooves in the wire may significantly increase the strength of the wire 12.

In an exemplary embodiment, wire 12 is comprised of a thin metal such as, for example, stainless steel, titanium and/or titanium alloy, so it may be easily cut to almost any desired length, thereby eliminating or reducing the need for fixed lengths screws. As such, the invention substantially reduces or eliminates the need for the inventory or availability of large screw sets or multiple screws. Moreover, because the system may include numerous materials, configurations and designs for either wire 12 or cap 20, the invention provides increased versatility because the physician is provided with multiple options and choices for wire 12 and cap 20 combinations.

Figure 2A:
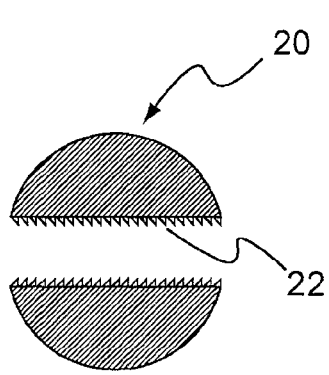
FIG. 2A is a quick cap in accordance with an exemplary embodiment of the present invention.
Figure 2B:
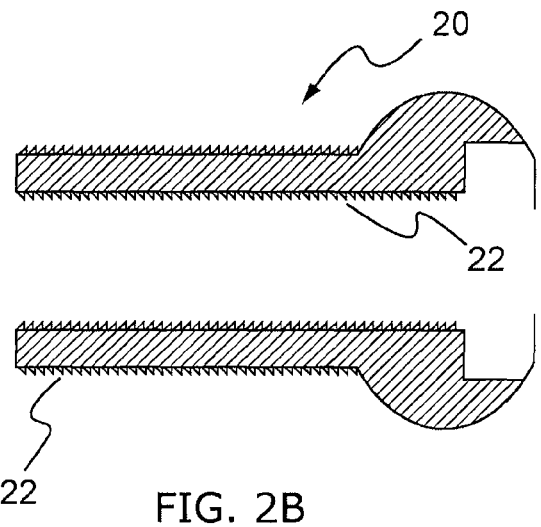
FIG. 2B is an alternative embodiment of a quick cap in accordance with an exemplary embodiment of the present invention.

Cap 20 is any device suitably configured to maintain or increase the pressure between the surfaces of pathology by limiting wire 12 movement. As shown in FIGS. 2A-2E, exemplary caps 20 may include various configurations, materials, shapes and/or sizes. In one embodiment, and as shown in FIG. 2A, cap 20 includes an inverse interface component 22 relative to wire 12 interface component such that cap 20 is restricted from backwards translation after cap 20 is inserted over wire 12. In one embodiment, the interface component 22 on cap 20 is located at least on the inside surface of the cap and includes a saw tooth pattern with the same or similar pitch as the saw tooth on wire 12. This configuration also allows cap 20 to slide along wire 12 without the need for spinning cap 20 which is important because time is of the essence in a medical procedure and spinning the cap down a sufficiently long length of wire would be very time-consuming. Examples of cap 20 include a screw cap 20, flat cap 20 and a quick cap 20.

Figure 2C:
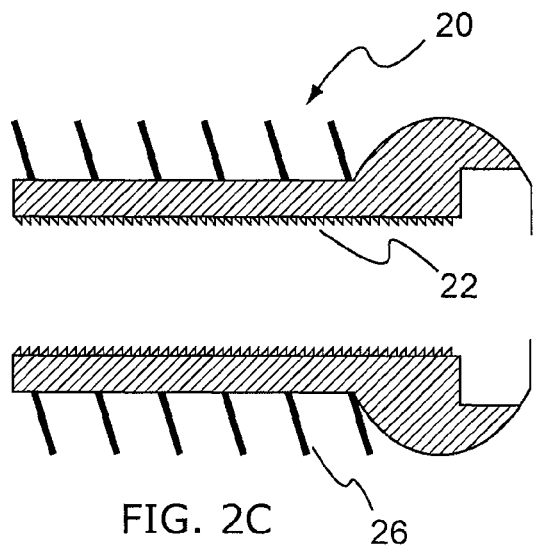
FIG. 2C is a screw cap in accordance with an exemplary embodiment of the present invention.
Figure 2D:
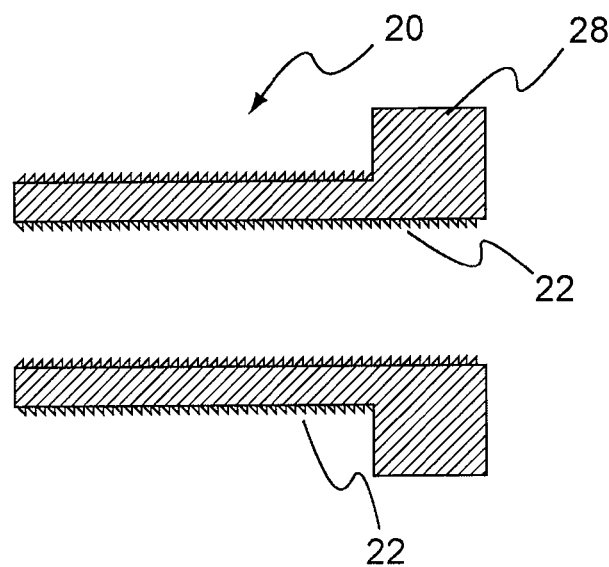
FIG. 2D is a flat cap in accordance with an exemplary embodiment of the present invention.

As shown in FIG. 2C, screw cap 20 is configured with teeth 22, cutting threads 24 and/or mating threads 26 on the outside surface to facilitate rotating cap 20 into the cortex to, for example, fix surgical plates against certain pathology. However, cutting threads 24 may not be needed on any of the caps because cutting threads 6 of head component 2 may have already tapped the threads on the inside surface of the bone, so the teeth 22 or mating threads 26 alone can simply rotatably engage the threads formed from cutting threads 6 and provide sufficient friction to secure the cap in the bone. As shown in FIG. 2D, flat cap 20 may include teeth 22, cutting threads 24 and/or mating threads 26 on the outside surface to facilitate rotating cap 20 into the cortex, but it also is configured with a flat top surface 28 to allow cap 20 to be inserted into the cortex such that the flat top surface 28 of cap 20 does not substantially protrude from the cortex surface. As best shown in FIG. 2A, for example, the quick cap 20 or any other cap may be configured with only the interface component on the inside surface, thereby allowing for quick and easy assembly.

Figure 2E:
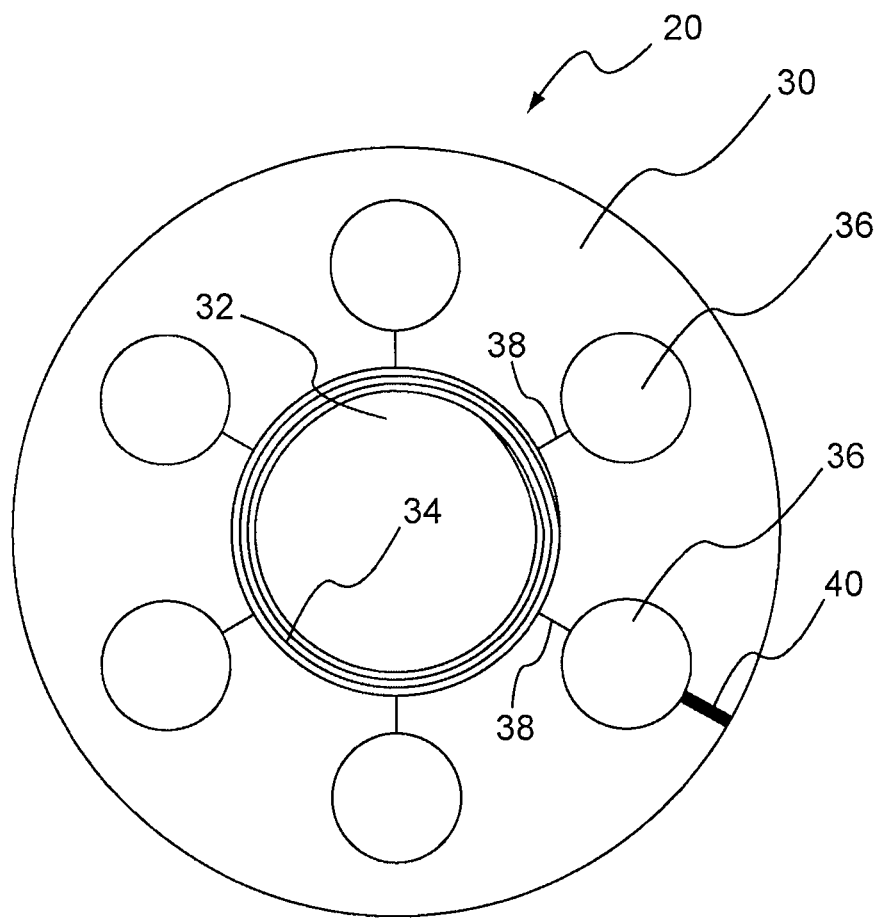
FIG. 2E is a top view of an alternative embodiment of a cap in accordance with an exemplary embodiment of the present invention.

With reference to FIG. 2E, in one embodiment, cap 20 is configured as a planar disk 30 with a center hole 32, wherein the center hole 32 includes an interface component 34 on its inner circumference surface. In an exemplary embodiment, the pitch of the saw tooth interface component is about 0.25 mm-0.5 mm. The planar disk 30 may also include any configuration for facilitating expansion of the disk 36 while sliding down wire 12. The configurations may include, for example, a cut 38 or a hole 36 in the planar disk 30. The planar disk may include multiple holes or cuts spaced over the planar surface. One or more of the additional holes 36 may also be connected to a cut 38 in the planar surface that extends to the center hole 32. One or more of the holes 36 may also be connected to a cut 40 in the planar surface that extends to the outside edge of the planar surface. In one embodiment, six additional holes 36 are evenly spaced around the planar surface with each hole 36 connected to a cut 38 which extends to the center hole, while one hole 36 also includes a cut 40 that extends to the outside edge of the planar surface.

The planar disk may also set inside a shallow cup device, wherein the circumference of the cup is slightly larger than the circumference of the planar ring in order to allow expansion of the ring. Moreover, a spring, or any other device suitably configured to apply pressure to cap 20, is placed between the planar ring and the cup device. In one embodiment, a bellville spring is used to apply pressure to the cap 20. The spring is configured to provide tension on wire 12 after resorption. During the healing process, cartilage forms at the break and the cartilage compresses, so bone resorption typically occurs at the location of the fracture. When tension on the lagwire is released due to bone resorption during healing, in one embodiment, cap 20 allows for auto tightening of the lagwire because micro-motions or vibrations will often cause cap interface device 22 to click down another notch on the inverse interface device of the wire 12.

Figure 2F:
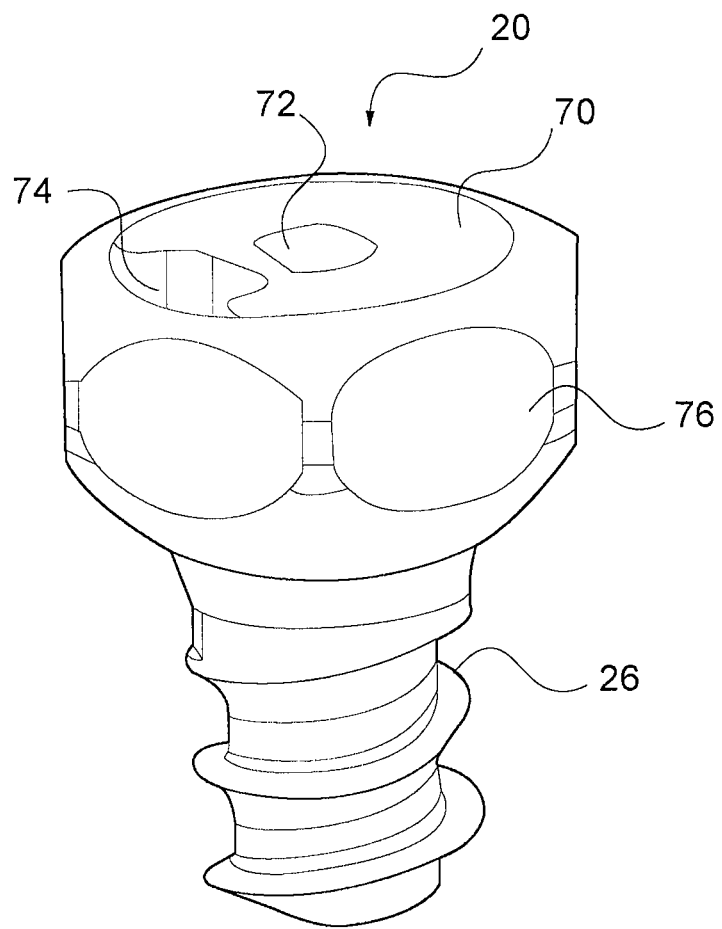
FIG. 2F is a perspective view of another embodiment of a cap in accordance with an exemplary embodiment of the present invention.
Figure 2G:
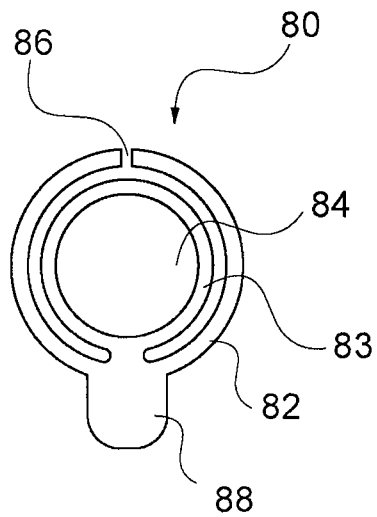
FIG. 2G is a top view of an exemplary tension spring in accordance with an exemplary embodiment of the present invention.

Another embodiment of a cap 20 is shown in FIG. 2F. As discussed above, cap 20 fits over one end of wire 12, such that cap 20 permits travel of cap 20 in one direction (e.g., distal travel with respect to the wire, toward the bone), but resists travel of cap 20 in the other direction (e.g., proximal travel with respect to the wire, away from the bone). In exemplary embodiments, cap 20 includes cutting threads 26, cover 70, a tension spring 80 and substantially flat surfaces 76 around the circumference of cap 20 to facilitate griping and/or turning cap 20. Cap 20 may be configured with a wider upper section which includes flat surfaces 76 around its circumference, and a tapered lower section with a gradually reducing diameter. Cutting threads 26 extend from the lower section. Cap 20 may include different thread configurations, lengths, diameters, pitches and the like to facilitate insertion into different types of bone or other structures (e.g., cortical bone, cancellous bone, etc).

Cover 70 may be integral with cap 20, or may be a separate component which is permanently or temporarily set in, or affixed to, cap 20. In one embodiment, cover 70 includes an opening 72 (e.g., in center of cover 70) which receives wire 12 and an inlet 74 which is configured to receive a component of extractor tool 90.

In one embodiment, tension spring 80 is set inside cap 20. In one embodiment, and with reference to FIG. 2G, tension spring 20 sits within cap 20 below cover 70; is circular; includes opening 84 (e.g., in center of circular ring) which receives wire 12; includes an outer ring 82 and an inner ring 83; includes a cut into, or non-connecting portion 86 of, outer ring 82 and/or inner ring 83; and/or includes a tab 88 which extends outward from outer ring 82. Outer ring 82 and an inner ring 83 may be one integrated ring, or two or more separate rings, which may not be connected, or may be connected in any manner.

At least a portion of inner ring 83 (or any portion of inner circumference of tension spring 80) provides greater friction against wire 12 one way (e.g., when the cap is pulled proximal, away from the bone). The friction is asserted against wire 12 because cover 70 impacts tab 88, so tab 88 forces tension spring 80 to flex, torque and/or tilt (e.g., 15 degrees) opening 84, thereby causing at least a portion of inner ring 83 to assert friction against at least a portion of wire 12. When cap 20 is pushed the other way (e.g., when the cap is pushed distal, toward the bone, using extractor 90), tab 88 is forced away from cover 70 and does not tilt, so it does not engage any surface, and the wire is able to translate, with minimal or no friction, through the central opening in the tension spring.

Figure 5A:
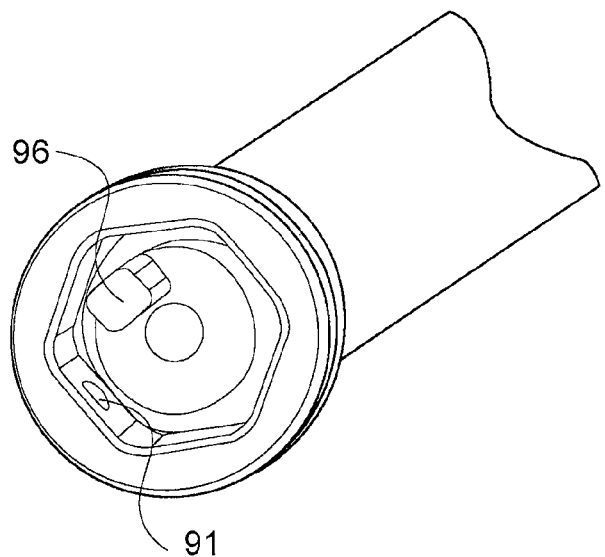
FIG. 5A is an exemplary head of the extractor of FIG. 5B in accordance with an exemplary embodiment of the present invention.
Figure 5B:
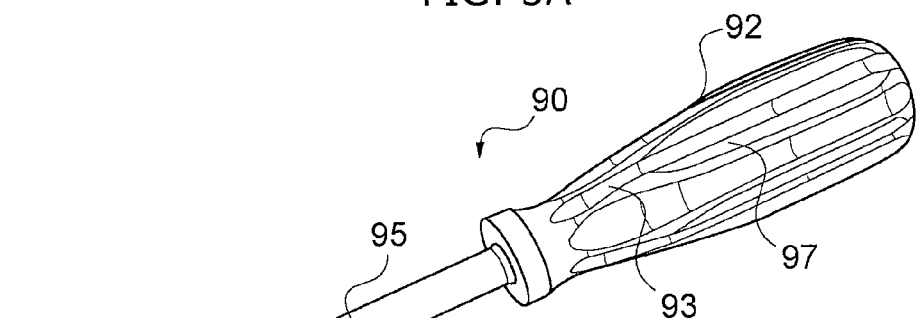
FIG. 5B is an exemplary extractor in accordance with an exemplary embodiment of the present invention.

Extractor/Driver 90, with reference to FIGS. 5A and 5B, includes any device suitably configured to insert and/or extract cap 20. In one embodiment, extractor 90 includes one or more ball bearings 91, shaft 95, shaft end 93, handle 92 which receives shaft end 93, tip sleeve 94, tip 96, and/or spring 97. Tip 96 may be the end of a long rod which extends upward into handle 92. Spring 97 applies pressure against the upper end of the rod that emanates from tip 96, thereby asserting a load against tip 96. Tip 96 is thus configured to be received into inlet 74 of cap 20 and the spring-load maintains tip 96 in inlet 74. Tip sleeve 94 is configured to receive cap 20 to also facilitate rotation and/or translation of cap 20. Tip 96 is mounted on a disc such that it allows tip sleeve 94 to more fully receive cap 20. The disc also rotates such that extractor 90 may rotate around cap 20, with minimal or no movement of tip 96. Ball bearings 91 are configured to facilitate rotation of tip sleeve 94 around outer surface of cap 20.

Figure 5C:
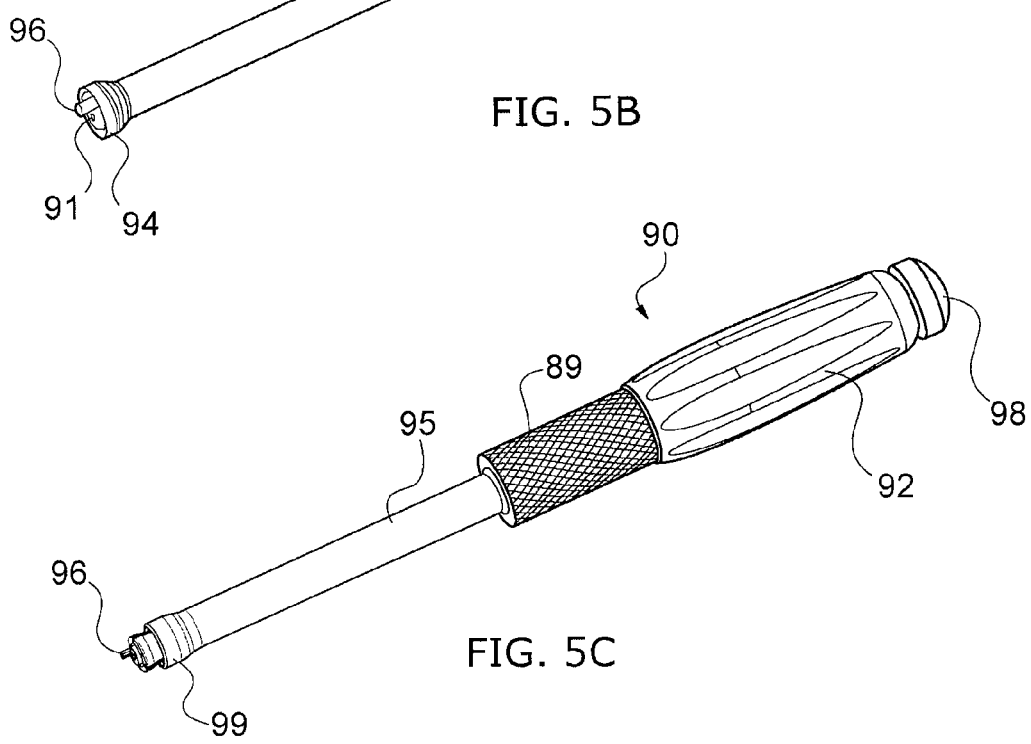
FIG. 5C is another embodiment of an exemplary extractor in accordance with an exemplary embodiment of the present invention.

Another embodiment of extractor/driver 90 is shown in FIG. 5C. In this alternative embodiment, the rod may have a first end which includes tip 96, and a second end 98 which may exit handle 92 such that the user may apply pressure to the second end 98 of the rod, thereby similarly applying pressure and a load against tip 96. Exit handle 92 also rotates such that it enables rotation of tip 96 which allows the user to rotate tip 96 until tip 96 mates with the inlet in cap 20. In another embodiment, collet sleeve 99 is attached to collet advancing handle 89. Collet advancing handle 89 includes a threaded inner surface which is configured to advance shaft 95, and thus, advance collet sleeve 99 forward over cap 20 to facilitate grasping of cap 20 for removal of cap 20.

Figure 3A:
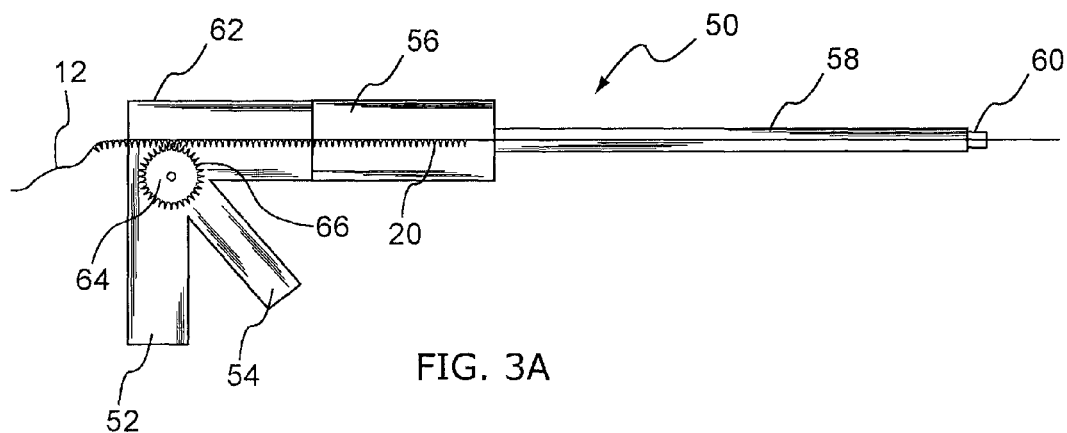
FIG. 3A is a tensioner in accordance with an exemplary embodiment of the present invention.

A tensioner 50 may also be used in conjunction with the present invention. With respect to FIG. 3A, tensioner 50 is any device suitably configured to insert a cap 20 into an object and/or provide tension to a wire 12. In one embodiment, tensioner 50 increases the pressure between the surfaces of pathology by providing tension to a wire 12 while the head component 2 of wire 12 is fixed into a bone or far cortex. In an exemplary embodiment, tensioner 50 includes a handle 52 with a hand trigger 54, wherein the handle 52 supports a rotatable barrel 56 which mates with a cylindrical rod 58. Cylindrical rod 58 may be cannulated to receive wire 12 and/or have a driver 60 (e.g., hex, phillips, screw, allen and/or the like) at its distal end for mating with the tool attachment 10 of head component 2. The barrel 56 may be rotated manually or automatically in order to rotate the driver 60 into the object (e.g., bone or cortex). In one embodiment, tensioner 50 includes a means for exerting a force on wire 12, such as, for example, internal gears 64, wherein the gears 64 include an interface component 66 (e.g., saw tooth) which mate with the inverse sawtooth 20 on wire 12. By pivoting the hand trigger 54, the internal gears are rotated such that the gears cause wire 12 to translate out the back end 62 of the tensioner 50, thereby exerting tension on wire 12 which is fixed at its distal end. The tensioner 50 may also include a gauge type device or any other device which is suitably configured to measure and/or display the tension exerted on wire 12.

Figure 3B:
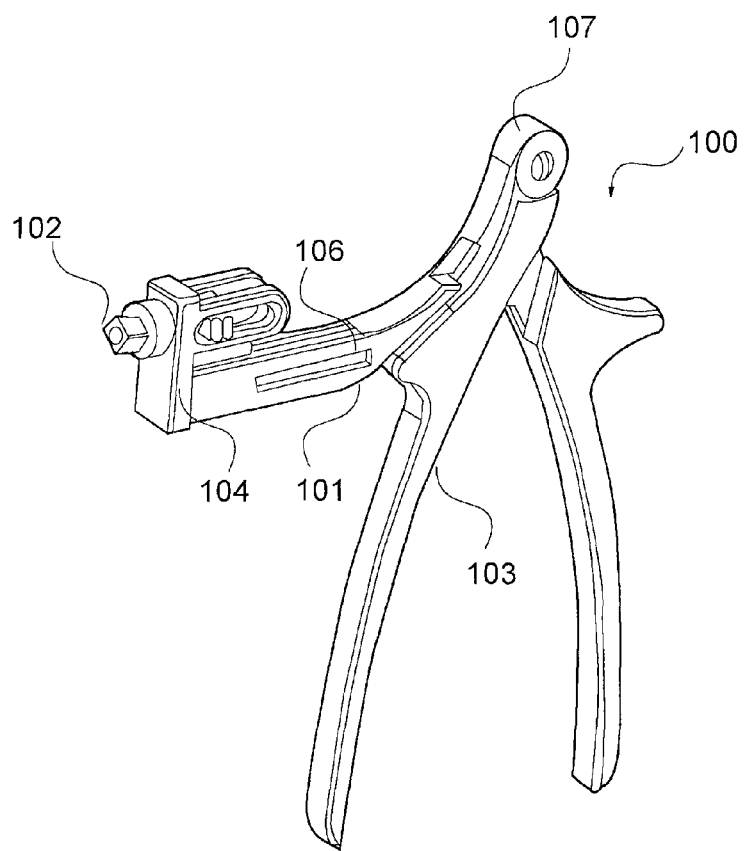
FIG. 3B is another embodiment of a tensioner in accordance with an exemplary embodiment of the present invention.

Another embodiment of a tensioner (e.g., tensioner 100) is shown in FIG. 3B. In one embodiment, tensioner 100 includes a base 101, a DVR connect component 102, a handle 103, a lock 104, and/or a spring link 106. Tensioner 100 is configured to accept multiple size wires and may include an indicator to show the amount of tension being applied. Tensioner 100 is also configured such that extractor 90 may clip into tensioner 100.

Figure 6:
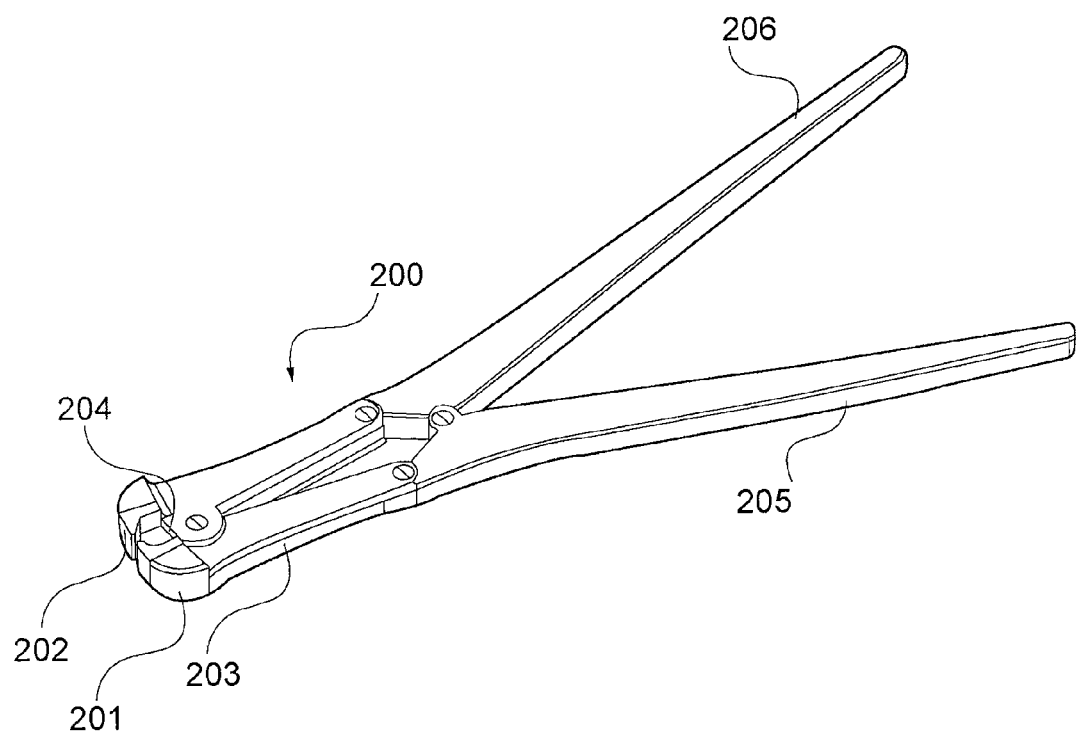
FIG. 6 is an exemplary cutter in accordance with an exemplary embodiment of the present invention.

After tensioning wire 12 to the desired tension, wire 12 may be cut, broken or shortened using any known device or method. With reference to FIG. 6, cutter 200 may be used. Cutter 200, in one embodiment, includes insert left 201, insert right 202, jaw left 203, jaw right 204, cutter left 205, and cutter right 206. Cutter 200 includes a cutting surface that extends beyond the main body of cutter 200 such that the wire may be cut from various angles.

The various components discussed herein can be suitably configured to perform the following method, wherein the steps can be performed in any order and any individual step is not necessary to the method. In an exemplary embodiment, a cannulated lagwire driver is suitably attached to a surgical drill, such that the drill allows for automatic rotation of the driver. The wire 12 of lagwire system 1 is placed into the channel of the driver such that the end of the driver encompasses or is received into driver head 10 of head component 2, thereby allowing wire 12 to be drilled into the bone. In one embodiment, head component 2 is configured with a hex head as the driver head 10 such that the driver suitably mates to the hex head. The head component 2 and wire 12 are then drilled into the bone to a desired depth using the automatic surgical drill (or any other manual or automatic device for rotating head component 2). Specifically, drill tip 4 of head component 2 facilitates the drilling of a pilot hole, wherein the proximal cutting threads 6 tap the bone for threading the inner surface of the hole, then the proximal mating threads 8 rotationally mate with the newly created threaded surface, thereby temporarily attaching the head component 2 into the cortex of the bone.

After attaching the head component 2 to the bone, the surgical drill is removed and a cap 20 is threaded onto the proximal end 14 of wire 12. Cap 20 is then translated distally along wire 12 until cap 20 contacts the bone or other desired pathology. In one embodiment, a lagwire tensioner is used to exert tension on the lagwire. In another embodiment, a lagwire tensioner 50 may be used to force or seat cap 20 into the bone surface or any other desired position. The hex head 60 of the tensioner 50 may be used to screw cap 20 into the bone surface. In another embodiment, the lagwire tensioner 50 exerts tension on the lagwire 12 up to a desired tension which may be read from a gauge communicating with the tensioner.

After positioning the lagwire device 1 and applying the appropriate amount of tension, in one embodiment, the excess wire 12 may be suitably removed by, for example, a wire cutter or any other suitable device. In another embodiment, a crimp type device may be placed on wire 12 to also help maintain tension. The crimp may include a clamp type device, bending the existing wire 12, screwing a nut onto the end of wire 12 and/or the like. The crimp may be placed on wire 12 after cap 20 is set in place, for example, in order to crimp other end pieces together. The tensioner 50 may also be used to reverse screw cap 20 in order to remove a wire 12 out of the bone. Moreover, in a situation where head component 2 strips out of the bone (for example, when the bone is of poor quality), the present invention allows the lagwire to be pushed through the opposite side of the bone and through the skin such that the head component 2 of wire 12 can be suitably removed (e.g., cut off) and a cap 20 can be placed onto that end of the lagwire, thereby resulting in better purchase (e.g., quality of fixation) of the bone.

Figure 4A:
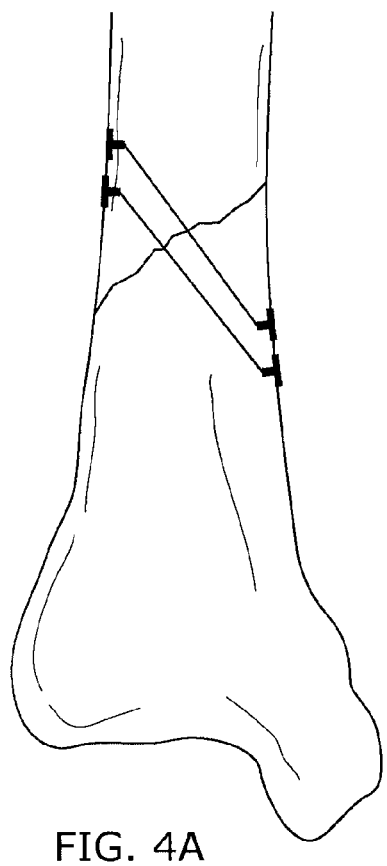
FIG. 4A is a fixation of a bone fracture in accordance with an exemplary embodiment of the present invention.
Figure 4B:
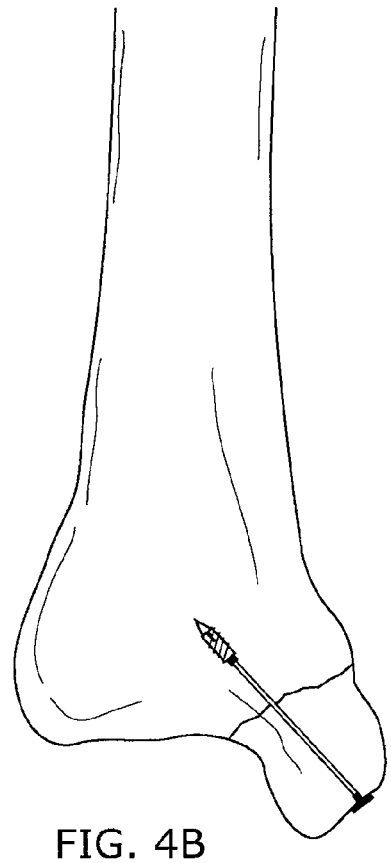
Figure 4C:
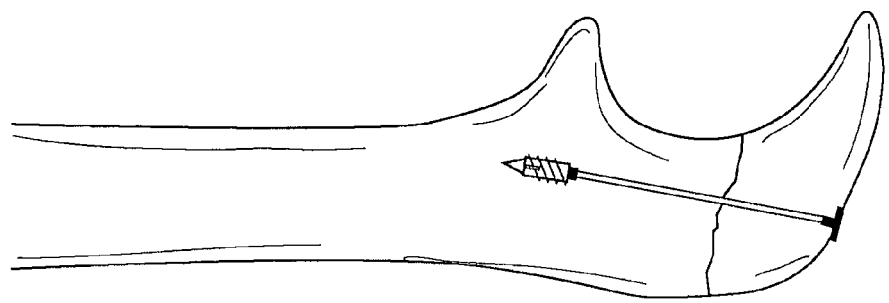

With respect to FIGS. 4A-4G, the lagwire system discussed herein can be used for the fixation of various types of bone fractures. FIG. 4A shows the use of the present invention for an exemplary fixation of a bone fracture or break. FIGS. 4B-4D show the use of the present invention for an exemplary fixation of fractures of certain portions of bones. Moreover, as shown in exemplary FIGS. 4F and 4G, the lagwire system 1 may also be used in a similar manner discussed herein in order to assist in holding a plate to the bone to help fix certain types of fractures. In other types of fractures, the lagwire may be placed through an entire limb to, for example, attach an external fixation device to the limb as shown in exemplary FIG. 4E.

Figure 4H:
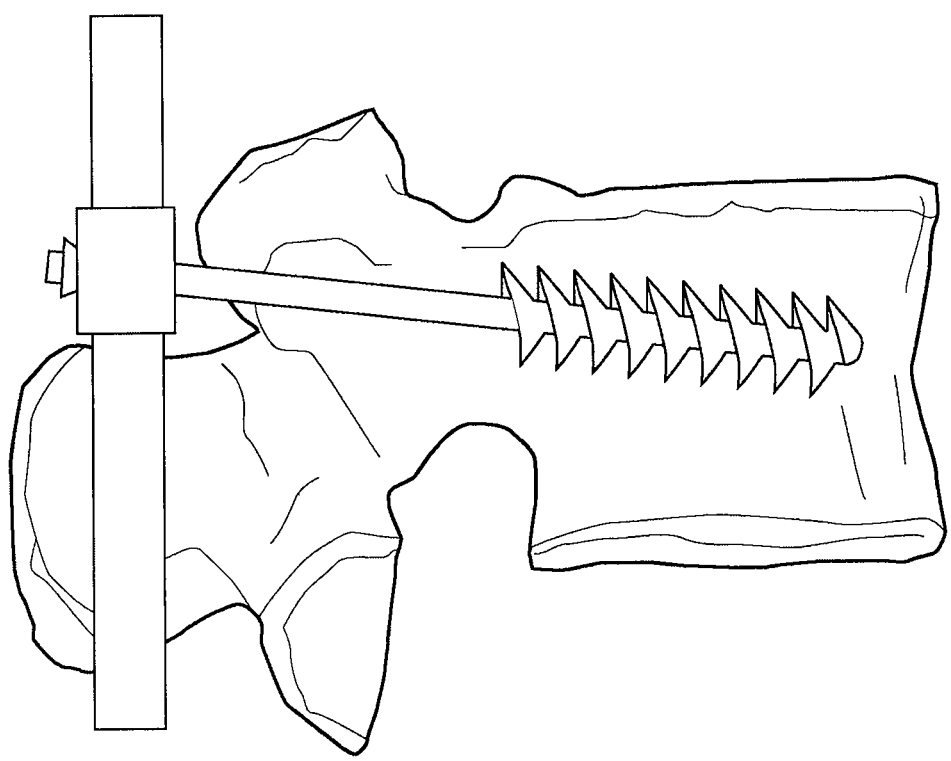
FIG. 4H is a fixation of a spinal injury in accordance with an exemplary embodiment of the present invention.

FIG. 4H shows a fixation of a vertebrae in accordance with an exemplary embodiment of the present invention. The screw is inserted into the vertebrae, then a cap is fitted onto the end of the wire. The cap is specially constructed such that the cap attaches to a rod. The rod may extend along various vertebrae such that the lagwires may extend from various vertebrae and all connect to the same rod. Another screw and lagwire may be inserted into the other side of the vertebrae such that the wire extends from the other side of the vertebrae and its cap connects to a second rod on the other side of the vertebrae for additional stability.

As described herein, the system and method of the present invention provides a device which is self-drilling, self-tapping and can be inserted under power. The invention also facilitates reducing and fixing fractures in one step. As such, the invention substantially expedites the process for fixation of bone fractures which is, of course, critical during trauma situations in order to stabilize a patient or to minimize the amount of time the patient is on the operating table or under anesthesia. In contrast to typical prior art screws wherein a gliding hole in the near cortex simply guides the screw, the present invention provides the ability for two sides of cortex lag screw fixation. Moreover, because of the strength of the attachment to the bone, the invention enables sufficient fixation even in poor quality bone material. Furthermore, wherein the prior art systems often require the use of cannulated screws in order to utilize a guidewire for placement, the present invention does not require the use of cannulated screws. Because the lagwire includes a tip 4 which creates a pilot hole, taps the bone for threads and fixes the threads into the bone, the system and method minimizes the possibility of inaccurate placement into the distal cortex or missing the distal hole.

In prior art systems, the physician typically cuts a relatively large opening in the skin in order to locate the bone segments, pull the bone segments into alignment, then place the screw into the bones. In the present invention, the system facilitates the percutaneus technique by allowing the physician to cut a minor incision into the skin for the head component, insert the head component, then pull the bones together with wire 12 and set the cap, all without large incisions or additional incisions.

The present invention is described herein in connection with the fixation of bone fractures; however, one skilled in the art will appreciate that the lagwire system or method described herein may also be used for changing, maintaining, reducing or expanding the distance between objects or surfaces, compressing objects together or providing pressure to surfaces. For example, the present invention may be used to repair wood products, tree limb damage, breaks in supports or columns, cracks in sculptures or buildings, breaks in sections of concrete or other building materials, cracks or breaks in car parts and/or the like.

In the foregoing specification, the invention has been described with reference to specific embodiments. Various modifications and changes can be made, however, without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", "includes", "including", or any other variations thereof, are intended to cover a non-exclusive inclusion, such that a process, method, article, or apparatus that comprises or includes a list of elements does not include only those elements but may include other elements not expressly listed or inherent to such process, method, article, or apparatus. Further, no element described herein is required for the practice of the invention unless expressly described as "essential" or "critical." Moreover, where a phrase similar to 'at least one of A, B, and C' is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

We claim:

1. A system for facilitating a change in distance between objects, said system including:
 a head component configured to attach to one of said objects;

a wire having a first end and a second end, wherein said first end of said wire is configured to mate with said head component;

a cap configured to mate with said second end of said wire, wherein said cap permits distal travel of said cap with respect to said wire, but resists proximal travel of said cap with respect to said wire, wherein said cap includes a tension spring which engages said wire, wherein said tension spring asserts friction against said wire in response to said cap being translated in one direction, but minimal friction against said wire in response to said cap being translated in an opposite direction; wherein said tension spring includes a tab joining and extending from an outer ring and an inner ring, wherein said inner ring is spaced radially from said outer ring; and a cover which encapsulates said tension spring within a head portion of said cap, wherein said cover contacts said tab causing said inner ring to at least one of flex, tilt or torque.

2. The system of claim 1, wherein each of said objects include at least one of bone and vertebra.

3. The system of claim 1, further including an extractor configured to at least one of rotate and translate said cap.

4. The system of claim 1, wherein said cap is configured with threads on an outside surface of said cap to facilitate rotating said cap into said object.

5. The system of claim 4, wherein said cap is configured with a substantially flat end to minimize said cap from protruding from said object surface.

6. The system of claim 5, wherein said cap includes a center hole for receiving said wire.

7. The system of claim 6 further including a tensioner for applying tension to said wire.

8. A cap device configured to mate with a first end of a wire, wherein said cap device includes:

a head portion;

a tension spring including an inner ring and an outer ring which are non-continuous over a substantial portion of an outer circumference of said inner ring and an inner circumference of said outer ring, wherein said tension spring is removably assembled within said head portion, wherein said tension spring asserts friction directly against said wire in response to said cap being translated in one direction, but minimal friction against said wire in response to said cap being translated in the opposite direction, wherein said tension spring includes a tab, wherein said tab is configured to force said tension spring to assert friction against said wire; wherein said tension spring includes said tab joining and extending from said outer ring and said inner ring, wherein said inner ring is spaced radially from said outer ring; and a cover which encapsulates said tension spring within said head portion, wherein said cover contacts said tab causing said inner ring to at least one of flex, tilt or torque.

9. The cap device of claim 8, wherein said cap device includes an outside surface, wherein at least a portion of said outside surface has cutting threads.

10. The cap device of claim 9, wherein a second end of said wire includes a head component configured to attach to a bone portion, wherein said wire is a flexible wire comprised of a thin metal.

11. The cap device of claim 10, wherein said tension spring includes a cut in a portion of said outer ring.

12. The cap device of claim 11, wherein said tension spring is configured to permit distal travel of said cap device with respect to said wire, but resists proximal travel of said cap device with respect to said wire.

\* \* \* \* \*